United States Patent [19]
Harman et al.

[11] Patent Number: 5,260,213
[45] Date of Patent: Nov. 9, 1993

[54] FUSED BIOCONTROL AGENTS

[75] Inventors: Gary E. Harman; Thomas E. Stasz; Norman F. Weeden, all of Geneva, N.Y.

[73] Assignee: Cornell Research Foundation, Inc., Ithaca, N.Y.

[21] Appl. No.: 597,119

[22] Filed: Oct. 16, 1990

Related U.S. Application Data

[63] Continuation of Ser. No. 244,444, Sep. 14, 1988, abandoned, which is a continuation-in-part of Ser. No. 34,304, Apr. 3, 1987, abandoned.

[51] Int. Cl.$^5$ ............... C12N 1/14; C12N 15/00; A01C 1/06; A01N 63/00
[52] U.S. Cl. ................. 435/254.6; 435/172.2; 435/945; 47/57.6; 424/930; 935/96; 935/97
[58] Field of Search ............ 435/172.2, 254, 945; 935/97, 96; 47/57.6, 58, 57.604; 424/93, 93 Q

[56] References Cited

U.S. PATENT DOCUMENTS 4,748,021  5/1988  Chet et al. ............... 424/93

OTHER PUBLICATIONS

Stasz et al. 1986, Phytopathology 76(10):1104, abstract #376.
Stasz et al., 1987, Phytopathology 77(12):1771.
Ogawa et al., 1987, Enzyme Microb. Technol. 9: 229-231.
Bojnanska et al., 1980, Asta Microbiol. Acad. Sci. Hung, 27: 305-307.
Picataggio et al., 1983, Eur. J. Appl. Microbiol. Biotechnol. 17: 121-128.
Gracheck, Abstract of Ph.D. Thesis, May 1984, University of Arkansas.
Hong et al. (1985) J. Nat. Acad. Sci. Repub. Korea Nat. Sci. Ser. 24(0): 53-90 (abstract cited).
Toyama et al. (1984) Appl. Environ. Microbiol. 47(2): 363-8.

*Primary Examiner*—David T. Fox

[57] ABSTRACT

Fused strains of Trichoderma spp described herein are useful as biocontrol agents to protect seeds, especially when used in conjunction with solid matrix priming or osmoconditioning.

4 Claims, 6 Drawing Sheets

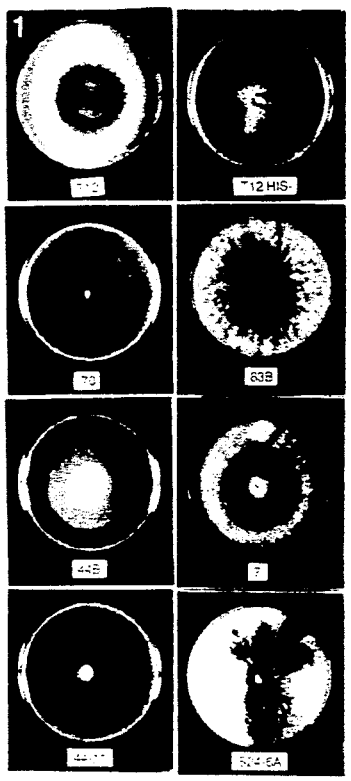
FIG. IA
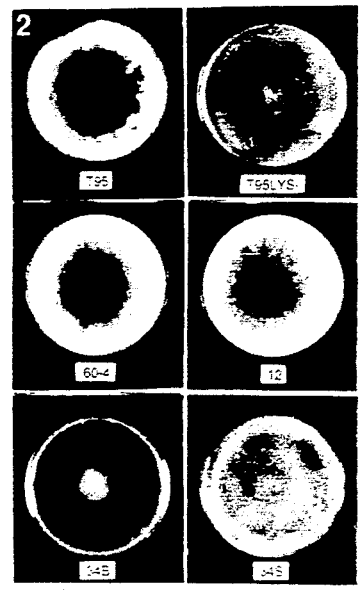
FIG. IB
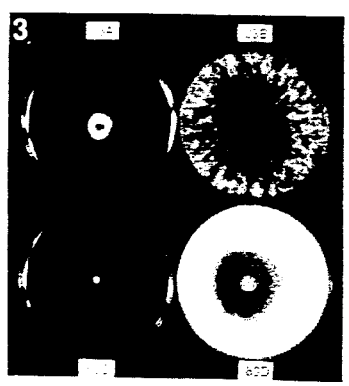
FIG. IC
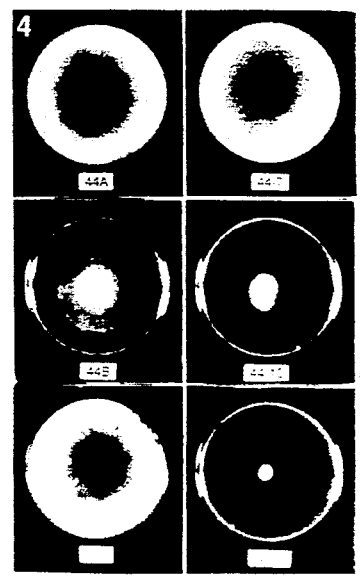
FIG. ID

FUSED BIOCONTROL AGENTS

CROSS-REFERENCE TO RELATED APPLICATION

This application is a continuation of application Ser. No. 07/244,444, filed Sep. 14, 1988, now abandoned, which is a continuation-in-part of application Ser. No. 07/034,304, filed Apr. 3, 1987, now abandoned.

BACKGROUND OF THE INVENTION

Biological control (biocontrol) of plant pathogens is becoming an important component of plan disease management. Biocontrol potentially offers answers to many persistent problems in agriculture, including those concerning resource limitations, nonsustainable agricultural systems and over-reliance on pesticides (Cook and Baker, 1983, *Am. Phytopathol. Soc.* St. Paul, Minn. 539 pp). Biocontrol agents are particularly attractive because they may be able to colonize and protect plant portions inaccessible to conventional chemical pesticides (e.g. plant roots in soil) (Harman and Hadar, 1983, *Seed Sci. and Technol.* 11:893–906; and Akhmad and Baker, *Phytopathology* (in press)). Much emphasis is now being placed on the purposeful application of specific biocontrol agents, as opposed to improving the level of naturally occurring biocontrol by environmental modification (Cook and Baker, 1983, supra). Many fungi and other microorganisms have been shown to control various plant pathogens, and a few fungal agents now are being used commercially on a limited scale in Europe to control specific pathogens, including *Botrytis cinerea* on grapes, *Ceratocystis ulmi* (Dutch elm disease) on elms, and *Chondrostsereum purpureum* (silver-leaf disease) on ornamental trees.

The successful use of Trichoderma species as biocontrol agents will be greatly enhanced if improved strains are developed. Five species (species aggregates) of *Trichoderma* (*T. hamatum, T. harzianum. T. koningii. T. polysporum* and *T. viride*) are most important for biocontrol (Cook and Baker, 1983, supra). However, biocontrol capability, as well as numerous other desirable or essential traits, is an attribute of specific strains, rather than of particular species or genera, and is extremely variable among strains. For example, most currently utilized strains are unable to grow at either high or low temperatures favored by some plant pathogenic fungi, only a few are rhizosphere competent (Ahmad and Baker, supra: Chao et al., 1986, *Phytopathology* 76:60–65), and most control only a narrow range of plant pathogens.

The strains presently available were obtained by selection from naturally occurring variation. Typically, large numbers of wild isolates are screened for their ability to control specific pathogens under controlled conditions. Mutation and further selection of strains has been also employed (Papavizas, 1985, *Annu. Rev. Phytopathol,* 23:23–54., Ahmad and Baker, 1987, supra).

Genetic recombination potentially is a much more powerful method for developing superior biological control strains than selection or mutation. Strains expressing desirable attributes can be used as parents in crosses with other strains expressing other desirable traits. By so doing, progeny with combinations of traits could be developed. Unfortunately, sexual stages are rare or lacking in most strains of Trichoderma spp., and conventional sexual crosses cannot be used to genetically manipulate these fungi.

Protoplast fusion may provide a means of genetically manipulating strains of Trichoderma spp. by initiating parasexuality (Anne and Peberdy, 1975, *Arch. Microbiol.* 105:201–205; Fincham et al., 1979. Fungal Genetics. 4th ed. Univ. Calif. Press, Berkeley. 636 pp). In fact, interspecific and even intergeneric crosses may be feasible. Intraspecific crosses have been accomplished in *Trichoderma reesei* (Gracheck, 1984, Protoplast formation, regeneration, and fusion in *Trichoderma,* Ph.D. Thesis, Univ. Arkansas.; Toyama et al., 1984, *Appl. Environ, Microbiol.* 47:363-368). Thus it may be possible to combine desirable traits from various parental strains to produce superior biocontrol strains.

BRIEF DESCRIPTION OF THE DRAWINGS

FIG. 1A (consisting of a photo identified in the upper left hand corner by the numeral 1, of a group of cultures) shows the appearance of the wild type T12, T12 his⁻, and various progeny strains derived from fusion of *Trichoderma harzianum* T12 his⁻ and T95 lys⁻. All strains shown are of the T12 isozyme phenotype. Cultures were grown in petri dishes 10 cm in diameter on potato dextrose agar for 6 days.

FIG. 1B (consisting of a photo identified in the upper left hand corner by the numeral 2, of a group of cultures) shows the appearance of the wild type T95, T95 lys⁻, and various progeny strains derived from fusion of *Trichoderma harzianum* T12 his⁻ T95 lys⁻. All strains shown are of the T95 isozyme phenotype. Cultures were grown in petri dishes 10 cm in diameter on potato dextrose agar for 6 days.

FIG. 1C (consisting of a photo identified in the upper left hand corner by the numeral 3, of a group of cultures) shows the variation in strains derived from sectors of strain 83. 83A, 83B, 83C are of T12 isozyme phenotype, while 83D is of T95 phenotype. Cultures were grown in petri dishes 10 cm in diameter on potato dextrose agar for 6 days.

FIG. 1D (consisting of a photo identified in the upper left hand corner by the numeral 4, of a group of cultures) shows the variation in strains derived from sectors (44A, 44B, 44C) or single spores (44-7, 44-10, 44-11) of strain 44. Strains 44A, 44C, and 44-7 are of the T95 isozyme phenotype, while 44B, 44-10, and 44-11 are of the T12 phenotype. Cultures were grown in petri dishes 8 cm in diameter on potato dextrose agar for 6 days.

In FIG. 2A, differences at day 3 and 5 are nonsignificant, while the Minimum Significant Difference at days 7 and 8 are, 40 and 42%, respectively, according to Waller and Duncan's K-ratio test (K-100).

FIG. 5A shows the appearance of cucumbers 9 d after planting from seeds treated with Pelgel alone, *Trichoderma harzianum* strains T12, T95, or 1295-22, all after solid matrix priming. In FIG. 5B is shown roots of the seedlings pictured in FIG. 5A.

DESCRIPTION OF THE INVENTION

Figure 2A:
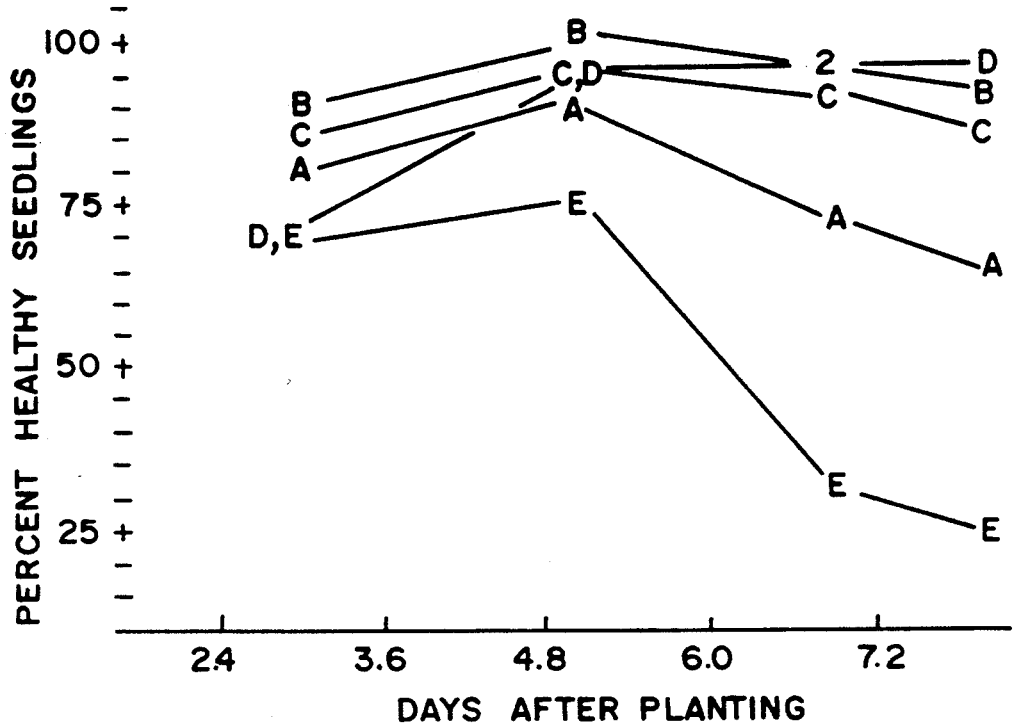
FIGS. 2A amd 2B graphically present the numbers of healthy seedling produced after treatment of cucumber seeds with strains of *Trichoderma harzianum* using solid matrix priming (A) or a conventional Methocel slurry (B) seed treatment. Strains used were the parental strain T12 (A), 1295-74 (B), 1295-7 (C), 1295-22 (D). and parental strain T95 (E).

Protoplasts from two strains of *Trichoderma harzianum* were fused and gave rise to numerous types of progeny strains. Rapid-growing sorts with an isozyme phenotype like that of the T12 parent are superior biocontrol agents. When cucumber seeds are treated with these strains in a solid.matrix priming system, nearly perfect stands are obtained when these seeds are planted in Pythium-infected soil. Seeds so treated produce seedlings that largely are unaffected by post-emergence damping off or root disease. Parental strains give rise to similarly large numbers of seedlings initially, but these are subject both to post-emergence damping off and to root disease. However, even seeds treated with the parental strains are better protected than if seeds are treated with the fungicide thiram. However, differences among strains largely are not seen when seeds are treated using a conventional methocel slurry. This lack of difference may result because Pythium spp. infect seeds very rapidly, and, in the methocel slurry treatment, Trichoderma spores of any strain may not germinate sufficiently rapidly to impede this early seed infection. In addition to providing excellent seed and seedling protection, one strain (1295-22) colonizes root surfaces well. This ability (rhizosphere competence) is a desirable attribute of biocontrol agent, since it allows agents to readily protect roots against attack by soil-borne fungi.

In copending application Ser. No. 034,813 now abandoned, entitled "Biological Control and Solid Matrix Priming", filed Apr. 4, 1987, there is described a process for priming or osmoconditioning seeds in the presence of biocontrol agents. In this process seeds in the presence of biocontrol agents are primed with water using a solid phase matrix rather than using aqueous solutions. The solid matrix comprises finely divided non plant pathogenic, water retaining solid material preferably a carbonaceous, most preferably lignateous solid which has a large equilibrium water potential $\psi$, and preferably has an osmotic potential component which is at least about 90% and preferably greater than 95% of the total water potential. Examples of such materials include coal, especially soft coal, lignateous shales such as the leonardite shale, sold as Agro-Lig, and sphagnum moss.

The solid matrix material, when containing the water necessary to prime the seeds in question, must still be sufficiently friable, nonclumping etc. so that when desired, it can be mechanically separated from the treated seeds after treatment without damage to the seeds. The particle size of the matrix material is not unduly critical, but for mechanical reasons should be smaller than seed being treated, e.g. usually less than about 20 mesh, but preferably substantially smaller. Typically a material less than about 60 mesh is preferred; for example, the Agro-Lig described hereinafter was 90% /wt less than 200 mesh; the soft coal was less than 60 mesh.

In the solid matrix priming process, the seed to be treated, a predetermined amount of the solid matrix material, and a predetermined amount of water are admixed and the mixture allowed to stand, preferably in a container which allows entry of air but which reduces evaporative losses, for example a closed container with a small top opening, for a time and at a temperature sufficient to allow the seeds to imbibe water from the matrix and come to a water content equilibrium sufficient to enhance emergence, growth or yield characteristics, but short of that which would cause the seed to sprout.

As in solution priming, the equilibrium amount of water for the system to prime the seed is dependent on the specific seed variety, its state or condition, and the water potential $\psi$ of the medium, here the solid matrix material. Typically the solid matrix material should have a water potential $\psi$ between about $-0.5$ to about $-2.0$ megapascal at equilibrium with the seeds. The seed priming art to some extent is still imperical, and while typical water amounts and media water potentials for a given seed type are already generally known in the art, it is frequently best to test a small seed sample over a readily determined range of water potentials and temperatures to determine what conditions of temperature, water potential and time cause maximum imbibing of water by the seed, short of sprouting of the seed.

In the preferred process of the invention a known weight of seed is wet with water and is also or has previously been inoculated with the biocontrol agent. The wetted seed in turn, is mixed with the dry, flowable, particulate solid matrix material, coating the wet seeds with the particulate matrix material. The remainder of the predetermined amount of water for osmoconditioning is then admixed with the coated seeds and the mixture held at a predetermined temperature usually between about 10° C. and about 25° C. for a time sufficient to allow the seeds to reach a desired moisture content equilibrium, usually one to about fourteen days.

It has now been discovered that when the biocontrol agents described herein, i.e. strains 1295-7, 1295-22, 1295-74 and 1295-106 are added to the solid matrix priming compositions in the conjoint process described in the pending application, they function in a significantly improved manner than when used alone. While not intending to be bound by these theories, it is presently believed that in the system of the invention the biological control agents themselves are primed or proliferate during the solid matrix priming and thus they are either more active or have more effectively colonized the seed coat surface prior to planting. What has been observed however is that post emergence damping-off was less, or more rapid emergence occurred, or more rapid growth was observed.

The biocontrol agent can be applied to the seed as a seed coat in a known fashion prior to the solid matrix priming step.

Typically the antagonist strains can be inoculated onto the seed in any manner known in the art, but for the purposes of this invention are usually applied as a suspension in water prior to solid matrix priming. (Though they could be applied by prior colonization on the solid matrix material in sufficient numbers so that when contacted with the seed sufficient numbers of antagonist would in turn establish themselves upon and coat the seed.)

When used independently as a seed coating typically about $10^8$ conidiospores of Trichoderma spp per ml are suspended in water and sufficient volume is used to ensure complete coverage of the seed surfaces this is usually 20 to 80 ml/kg of seed, the amount varying with the weight/surface ratio of the particular seed.

When used in conjunction with the solid matrix priming step the conidiospores can be added to the water used to initially wet the seed.

The seed that can be treated can be virtually any seed that benefits from osmoconditioning including most vegetable crops, and ornamental and agronomic crops. Included are cucumbers, lettuce, carrot, onion, melon, sweet corn, tomatoes, egg plant, peppers, flower seeds and alfafa.

Alternatively, fused strains of this invention can be inoculated onto or into the seed of the plant to be protected by means of a seed treatment or coat in any manner known in the art. Generally seed treatment formulations comprise a liquid or particulate vehicle such as an inert liquid or inert dust or powder containing the active antagonist. Preferably the seed treatment or coating contains an ingredient which assists the antagonists to penetrate or stick to the seed being treated. Examples of commercially available stickers include Methocel A4C (Dow Chemical Co.) or Pelgel (Nitragin Co.). Typically, spores or other propagules of the active antagonist are mixed with a viscous suspension of a sticker in water, and are then applied to the seed. Best results are obtained when about $10^8$ conidiospores of the Trichoderma spp. or about $10^{10}$ cells of *Enterobacter cloacae* are suspended in 10% (w/v) Pelgel or 2% (w/v) Methocel. Preferably, sufficient volumes of one of these mixtures are used to ensure complete coverage of the seed surfaces. These usually require, for example, about 20 ml/kg of seed to about 80 ml/kg of seeds, the necessary amount varying with the weight-surface ratio of the particular seed.

The fused strains are employed in an amount and in a manner to prevent or retard, that is control, the attack of a soil borne pathogen on the seed being protected.

When employed in a seed drill fluid, the fluid generally comprises a solution of a water soluble polymer. The polymer when dispersed in water increases the viscosity of the solution. The viscous solution or gel serves to suspend seeds, protects hydrated/germinated seeds from mechanical damage during sowing and acts as a lubricant to facilitate seed movement in the planter.

Polymers which can be employed to prepare seed drill fluids include hydroxyethyl cellulose, synthetic magnesium silicate clays, polyacrylamide and starch graft polymers other polymers known in the art may also be employed in a manner known in the art. Those polymers which are non-ionic are best suited as a carrier for the biological control organisms of the invention. Non-ionic gels are stable over a wide pH range, have little pH buffering and are generally stable with the addition of organic or unorganic chemicals.

The amount of the fused strain typically employed in a seed drill fluid is generally at least about $10^8$ spores/ml.

Although not presently recommended, the antagonists of the invention can be used in any manner which effectively innoculated the seed biosphere; for example if desired the antagonists of this invention could be broadcast or furrow applied.

If desired, the seeds and/or the priming mixture can be pH adjusted for maximum biocontrol agent effectiveness.

As is evident from the Examples, the fused Trichoderma strain of the invention and especially 1295-22 and 1295-106 are broad spectrum fungicide; a fact uncommon and unexpected when the typical naturally occurring Trichodermas are surveyed. All the strains of the invention are active against; for example, *Phythium ultimum, Phizoctonia solani, Fursaium graininearum,* and *Sclerotuim rolfsii.*

EXAMPLE 1

Media Several media were used. These included the basal medium (BM) of Toyama, 1984, supra, which contained 2.8 g/l $(NH_4)_2SO_4$, 600 mg/l urea, 4 g/l $KH_2PO_4$, 600 mg/l $CaCl_2\ 2H_2O$, 40 g glucose, 200 mg/l $MgSO_4$, 10 mg/l $FeSO_4\ 7H_2O$, 2.8 mg/l $ZnSO_4\ H_2O$, 3.2 mg/l $MnSO_4\ H_2O$, 4 mg/l $CoCl\ 6H_2O$, and 20 g agar. All components except the agar were dissolved water at a 2x concentration, and filter-sterilized by passage through a 0.45 μm filter. The agar was sterilized by autoclaving the two components. They were then brought to 60° C., mixed, and poured into petri dishes. Addition of 10% w/v sucrose as an osmiticant resulted in protoplast regeneration medium (PRM). The media amended with either 150 μg/ml histidine, 150 μg/ml leucine, or the combination, and were designated as BM+L, BM+H, or PRM+L, PRM+H, or PRM+HL for the basal or the protoplast regeneration medium plus these amino acids, respectively.

In addition Difco potato dextrose agar and broth (PDA and PDB, respectively) were used, as well as PDA amended with amino acids and/or 10 μg/ml benomyl, to give PDA+H, PDA+L, PDA+HL, or PDA+HLB. Benomyl was suspended in 10 ml sterile water and added to sterile medium cooled to 60° C., prior to pouring.

Strains used. Parental strains of *Trichoderma harzianum* Rifai were T95 (Ahmad and Baker, 1986, supra; American Type Culture Collection [ATCC] 60850) and T12m (Hadar et al., 1984, *Phytopathology* 74 106–110; ATCC 20737). T95 was a mutant resistant to benomyl at 50 μg/ml (ben+), while growth of T12 was prevented by 3 μg/ml benomyl (ben−). Auxotrophic mutants requiring lysine or histidine (T95 lys−, T95 his−, and T12 his−) were prepared by irradiating conidia with ultraviolet irradiation from a 15 watt germicidal fluorescent lamp until ca 99% of the conidia were killed. Irradiated conidia were transferred to a broth prepared from BM, but without agar. This mixture was incubated with shaking at 25° C. for 1 week and was filtered daily through four layers of sterile cheesecloth to remove germinated prototrophic conidia. The nongerminated conidia were then plated on BM+HL containing 0.1% w/v Igepal Co630 as a colony restrictor (Norton and Harman, 1985, *Can. J. bot.* 63:1040–1045), and incubated at 25° C. until colonies developed. These colonies were then individually transferred back to BM, and colonies that did not grow on this medium tentatively were considered to be auxotrophs. Identity of auxotrophs were confirmed by inability to grow on BM, but ability to grow on BM+H or BM+L. Once auxotrophs were found, they were single-spored to obtain homogenous and stable auxotrophs. Only auxotrophs that gave no growth upon repeated transfers to BM from actively-growing colonies BM+H or BM+L were used further. Plating of conidia from auxotrophs gave reversion frequencies of one in $10^{10}$ or less.

Isozyme analysis. Additional genetic markers were identified by subjecting extracts to horizontal starch gel electrophoresis followed by specific enzyme stains. For this purpose, cultures were grown in 10 ml of PDB in 25 ml flasks for 3-5 days at 25° C. on a reciprocating shaker. Resulting thalli (appx. 50 mg dry weight) were removed from flasks, dried briefly on filter paper, and placed in about 0.2 ml ice-cold extraction buffer (0.05M tris (hydroxymethyl) aminomethane—HCl pH 7.1). Two gel buffer systems were used for the analysis, these were the histidine gel system at pH 6.5 described by Cardy et al., 1972. Techniques for starch gel electrophoresis of enzymes from maize (*Zea mays L.*). Dept. of Statistics Mimeo Series No. 1317, North Carolina State University, Raleigh, N.C., and the tris citrate/-lithium borate system of Selander et al., 1971. Univ. Texas Publ. 7103:49–90. The procedure for electrophoretic analysis of the extracts was described by Weeden, 1984, *Euphytica* 33:199–208. Strains T12 and T95 were screened for reproducible differences in isozymic mobility on about 70 enzyme systems, using the procedures described by Weeden, 1984, supra. Of these, four were found to give reproducible and clearly resolved differences between strains T95 and T12. These enzymes were fumarase (FUM, E.C. 4.2.1.2.), phosphoglucomutase (PGM, E.C. 2.75.1) α-D-glucosidase (GLU, E.C. 3.2.1.20), and triosephosphate isomerase (TPI, E.C. 5.3.1.1). The histidine gel system was used for FUM, PGM, and GLU, while the tris-citrate/lithium borate system was used with TPI. Visualization of enzyme activity was accomplished using the assay systems described by Weeden and Gottlieb 1980, *Plant Physiol.* 66:400–403 for PGM and TPI, except that assay mixtures were applied as agar overlays. The method of Brewer 1970. An Introduction to Isozyme Techniques. Academic Press, New York, N.Y. 186 pp was used for FUM. A modification of the assay described by Smith 1976. Starch gel electrophoresis. In Chromatographic and Electrophoretic Techniques. Vol II, Yearbook Medical Publishers Inc. Chicago, pp 153–209 that contained 0.1M tris-HCl pH 7.1 and 3 mM 4-methylumbelliferyl αD-glucoside was used for GLU.

Protoplast isolation. Various procedures were evaluated to obtain high yields of viable protoplasts. We attempted to isolate protoplasts from immature conidia (Toyama et al., 1984, supra), from germinating conidia, and from young nonsporulating thalli.

Immature (nonpigmented) conidia were harvested from the advancing edge of colonies on PDA, suspended in sterile water and filtered through lens paper to free the conidia of hyphal debris. Conidial suspensions were mixed with 10% β-glucuronidase type H2, 10 mg/ml drieselase, 25 μg/ml chitase (Sigma Chemicals, St. Louis, Mo.) and 0.6M sucrose (Stasz and Harman, 1985, *Phytopathology* 75:1327), and incubated at 30° C. To isolate protoplasts from germinated conidia, mature conidia were placed in 200 ml of PDB amended with 1.5% w/v yeast extract and incubated for 16 hours 25° C. with shaking. Germinated conidia were collected by filtration onto Miracloth (Calbiochem, La Jolla, Calif.) in a Buchner funnel, and appx. $10^6$–$10^7$ were asceptically transferred either to 20 ml of the enzyme mixture described above, or to a mixture containing 13 mg/ml NovoZym 234 (Novo Laboratories, Wilton, Conn.) in 0.7M NaCl, and incubated for 24 hours at 30° C. with gentle shaking. Finally, protoplast isolation from young mycelium was tested by transferring appx. 100 small squares (2–4 mm$^2$) from young, nonsporulating colonies on PDA to 200 ml of the PDB plus yeast extract medium described above, and incubating these overnight with shaking at 25° C. to give spherical thalli, each about 4–6 mm in diameter. These were collected on Miracloth and incubated 24 hours in 80 ml of the NovoZym-NaCl mixture described above.

In all cases, protoplast-enzyme mixtures were filtered aseptically through 4 layers of cheesecloth to remove hyphae and other debris, and protoplasts were harvested by centrifugation at 100 xg for 5 minutes. Protoplasts were resuspended and washed in a variety of media, including PBS (0.01 NaPO$_4$ pH 7.0 plus 0.7M NaCl) or STC (0.6M sorbitol, 0.01M tris-HCl, and 0.01M CaCl$_2$ all at pH 7.5) (modified from Turgeon et al., 1985, *Molec. Gen. Genet.* 201:450–453). A number of inorganic salts were substituted for the sorbitol osmoticant in STC, including 0.7M NaCl, 0.6M M$_9$SO$_4$, 1.2M M$_9$SO$_4$, 0.6M KCl, 0.4M (NH$_4$)$_2$SO$_4$, 0.6M mannitol, and 0.6M sucrose.

Numbers of viable protoplasts in suspensions were determined by preparing stepwise dilutions in one of the suspension media (usually STC) described above, and then plating on PRM. Colonies typically developed from protoplasts with 48 hours of plating at 25° C. Protoplasts were distinguished from spores and hyphal fragments by preparing similar dilution series in distilled water, followed by plating on PRM. Protoplasts rupture upon exposure to water, while walled propagules do not. In all cases, numbers of colonies developing on PRM were compared with total numbers of protoplasts as determined by counts in a Petroff-Hausser bacterial counting chamber (Thomas Scientific, Swedesboro, N.J.).

Microscopic observation of nuclei. Determination of the number of nucli present in various cells was accomplished by fixing cells for 30 minutes in 3% formaldehyde dissolved in 50 mM sodium phosphate buffer at pH 7. Cells were then washed twice in the phosphate buffer, stained by adding 0.1 g/ml 4'-6-diamidino-2-phenyldihydrochloride (DAPI), and then rinsed twice again with phosphate buffer. Specimens so prepared were viewed using epiflourescent illumination on a Bausch and Lomb microscope equipped with an exciter filter passing light between 300 and 400 nm, a dichroic reflector reflecting light below 450 mm, and a barrier filter passing light above 475 nm. DAPI has a high specificity for staining DNA (Shapiro, 1985. Practical Flow Cytometry. Alan R. Liss, Inc., New York, N.Y. 295 pp).

Protoplast Fusion. Protoplasts were fused using a procedure similar to that described by Turgeon et al., 1985, supra. One ml of a suspension containing about $10^8$ protoplasts in STC were prepared with about that contained equal numbers of protoplasts from each parental strain. To this was added 200 μl of solution containing 60% (w/v) polyethylene glycol (PEG) solution (appx. molecular weight 3350, Sigma Chemical Co., St. Louis, Mo.), 10 mM $CaCl_2$, and 10 mM tris-HCl, pH 7.5. The PEG was mixed with the protoplast suspension by gently rolling the tube. A second 500 μl aliquot of the PEG solution was added, the mixture again gently mixed, and finally a third 500 μl aliquot was added and mixed by rolling. Following incubation at 30° C. for 10 minutes, the mixture was then diluted with 1.1 ml of STC, the mixture mixed gently, This dilution step was repeated, and finally 2.2 ml of STC were added. After fusion and dilution, protoplasts were recovered by centrifugation and resuspended in 5 ml STC.

Protoplasts from T95 his⁻ with protoplasts from T95 lys⁻ and T12 his⁻ with T95 lys⁻ were fused. As checks for possible reversion, each parental line was fused with itself. Protoplast suspensions were serially diluted in STC or in water and then plated on PRM. Serial dilutions from all fusions were plated on PRM+HL to determine the total number of viable protoplasts in each experiment.

Analyses of Progeny. After fusion of T95 lys⁻ with T95 his⁻, thalli developing on PRM were transferred to BM to eliminate the possibility of cross-feeding that may have occurred when heavy protoplast suspensions were applied to plates. Whether prototrophic progeny were heterokaryotic or had resulted from nuclear fusion was tested. Because each conidium receives only a single nucleus from the conidiophore (Picataggio et al., 1984, *Eur. J. Appl. Microbiol. Biotechnol.* 17:121-128; Toyama et al., 1984, supra) dissimilar nuclei segregate during conidiation. Conidia from progeny strains were suspended in water, filtered through a 5 μm pore size filter (Acrodiscs, VWR, Rochester, N.Y.) to remove hyphal fragments and dilutions were plated on BM, BM+H, BM+L, and BM+HL. In order to determine whether colonies that developed on BM were diploids, or whether they were derived from a conidium or other propagule containing two nuclear types, conidia were again isolated from these strains, filtered, and again plated on the array of media noted above.

With the T12 his⁻ plus T95 lys⁻ cross, a more complete genetic analysis could be conducted. Thalli developing on PRM were transferred to BM to eliminate the possibility of cross-feeding that may have occurred when heavy protoplast suspensions were applied to plates. After colonies reached a diameter of J5 mm in diameter, portions were transferred to 10 ml PDB in 25 ml flasks for isozyme analysis, and to BM, BM+H, BM+L, BM+HL, PDA+HL, and PDA+HLB. Additionally, conidia were harvested, filtered through a 5 μm filter, and plated on the media noted above. Numbers of colonies and appearance of colonies derived from single conidia were noted, and representatives of each colony type were tested on the isozyme assay system. In addition, sectors were frequently noted in colonies of progeny from this cross. These were analyzed by their ability to grow on the media noted above and by their isozyme phenotypes.

RESULTS

Protoplast preparation. Initial attempts to prepare protoplasts were conducted with immature or mature conidia. Enzyme preparations tested included the driesalase, glucuronidase, and chitinase mixture described above, the mixture modified to contain five-fold more chitinase, each of the enzymes alone, and NovoZym 234. Conidia were treated for up to 6 hours, were then placed in either water or STC, and numbers of cells were counted in a Petroff-Hausser microbiological counting chamber to determine numbers of osmotically-sensitive or insensitive cells. In no case were preparations obtained with more than 50% osmotically-sensitive cells (protoplasts). The most effective enzyme preparation was the mixture containing five-fold additional chitinase. Individual enzymes (chitinase, driesalase, β-glucuronidase, or NovoZym 234) gave fewer than 10% osmotically-sensitive cells.

Since protoplast yields were low with conidial suspensions, the liberation of protoplasts from young thalli or conidial germlings was investigated using Grachek's (1984) procedure. Either germlings or young thalli gave high yields (appx. $10^8$/flask) of protoplasts. At least 99% of these were osmotically sensitive; in some batches 99.99% were sensitive, as measured by growth on PRM after aliquots were diluted either in water or in STC. On PRM, visible thalli developed after 48 hours inocultation at 25° C. Protoplasts were released more rapidly from T95 than from T12; equivalent numbers of protoplasts were released from T95 after 90 minutes incubation as were released from T12 after 180 minutes.

Viability of protoplasts were determined by comparisons of counts of protoplasts in Petroff-Hausser chambers with plating on PRM. When protoplasts were suspended in STC, or in the similar mixtures but with various inorganic salts or sugars substituted for 0.6M sorbitol, about 10% of the protoplasts formed thalli. If however, PBS was used as the suspension medium, protoplasts did not regenerate. In all further work, STC was used as the suspension medium, and all protoplasts were prepared from young thalli.

Numbers of nuclei per propagule. Two to twelve nuclei were observed in protoplasts prepared from thalli, from germlings, or from immature conidia. Similar numbers of nuclei were observed in conidia.

Fusion between T95 his⁻ and T95 lys⁻. As a test of procedures developed, protoplasts of two auxotrophs of the same parental strain were fused. Fusion occurred between two cells, but aggregates of several cells were formed more frequently. Fused protoplasts were plated on PRM+HL or on PRM. On PRM+HL, $5\times10^5$ thalli arose from the fused protoplast mixture, while on PRM, $5\times10^4$ colonies developed. so the fusion frequency was about 10%. As a control T95 lys⁻ was fused with itself, as was T95 his⁻, and these also were plated on PRM or PRM+HL. On PRM, no colonies developed, while on PRM+HL, $28\times10^4$ and $10\times10^5$ colonies developed from T95 lys⁻ and T95 his⁻, respectively. On all media, visible thalli developed after 48 hour incubation. Fusion aggregates of two to many cells all gave rise to thalli, as determined by microscopic observation.

These results demonstrate that the colonies that grew on PRM after fusion between T95 lys⁻ and T95 his⁻ are prototrophic as a consequence of complementation between the fused parental strains. However, complementation may be due either to heterokaryosis or as a consequence of karyogamy. Therefore, conidial suspensions from twelve prototrophic progeny from this cross were diluted and plated on PRM, PRM+H, PRM+L, or PRM+HL. Dilutions on PRM+L, PRM+H, or PRM+HL gave $10^4$-$10^5$ thalli, while on PRM alone 0-2 thalli were recovered. These few prototrophic strains were allowed to sporulate, and conidia from these plated on the various media, and again, we obtained only about 1 prototrophic thallus per $10^5$–$10^6$ that were plated. This experiment was repeated twice with similar results.

Fusion between T95 lys⁻ and T12 his⁻. Strains T95 lys⁻ and T12 his⁻ were fused in two separate experiments. In both cases, thalli developed on PRM very slowly. The first thalli became visible after 1-2 weeks incubation, and even 5 weeks after fusion, new thalli were developing. These thalli were transferred to fresh BM, and upon development of a visible thallus, were assigned a number. From the first fusion, about 100 strains were harvested, while from the second about 20 were obtained and investigated further. These were tested for their isozyme patterns, and except for two (strains 12 and 34) all were identical to the pattern of the T12 parent. Additive combinations of bands indicative of heterozygotes was not observed for any strain.

As cultures were incubated on BM, more rapid-growing sectors arose. These were transferred to fresh BM plates and were designated with a letter designation, e.g. strain 44A or 44B for two sectors of strain 44 differing in growth rates or colony morphology. Some of these, when subjected to electrophoresis, gave isozyme patterns like those of the T12 parent and some were like that of T95. Again, double banding patterns were not observed.

Colony morphology and growth rates of these progeny strains were extremely variable. Two strains (7 and 22) eventually gave rise to cultures growing more rapidly than either parent on BM, others grew as fast as the original parents, while still others grew much more slowly (FIG. 1A). Colony morphology ranged from small, wrinkled, dark-brown pigmented strains with very sparse sporulation (e.g. strain 83A in FIG. 1A to ones that resembled one or the other wild-type parents (strains 12 and 7 in FIGS. 1A and 2, Table 1). FIG. 1A shows a range of colony morphologies and growth of strains with the T12 enzyme phenotype on a permissive medium (PDA) relative to the wild-type and auxotrophic T12 parents. FIG. 1B shows a similar assay among strains with the T95 enzyme phenotype.

Strains were grown on a range of media (BM, BM+H, BM+L, BM+HL, DA, PDA+HLB) to define their nutritional requirements and resistance to benomyl. These data are summarized in Table 1 for selected strains, along with their colony morphologies. All strains originally grew slowly on BM, but some sectored to give rise to fast-growing, fully prototrophic strains (e.g. 7, 12, 44A and several others). Others were very different in colony morphology than either parent (FIG. 1A, Table 1). Some (e.g. 34, 83A, B, or C) were not recognizable as Trichoderma spp.; however their enzyme phenotype matched that of one or the other parental type.

Similarly, variation was noted when single spores were plated on the various media and distinct colony morphologies could be selected. Strain 24, for example, gave rise to at least three distinct categories of subprogeny, i.e. a weakly prototrophic white colony that sporulated very little (Table 1), a type similar in all respects to the original T12 his⁻, and a rare type (appx 1 in $10^5$) that was similar to T95 in all respects, including isozyme phenotype. Two other strains similar in all respects to T12 his⁻ produced conidia that gave rise to subprogeny similar in all respects to T95.

As a consequence of sectoring and single-spore isolations, families of progeny strains were obtained that arose from the same original thallus, but which differ markedly in all characteristics measured. Examples of these are given in FIGS. 31C and 41C. Sectors from strain 83 (FIG. 1C) gave rise to slow-growing, wrinkled, nearly asporulent brown strains (83A or C) (the pigmentation became more intense as incubation was prolonged) and a more rapid-growing pinnate strain (83B), all of which have the T12 isozyme phenotype. Strain 83D, conversely, grew rapidly, sporulated well and was of the T95 isozyme phenotype. These characteristics were transmitted through conidiation (Table 1). Strain 44 originally was a slow-growing strain with the T12 phenotype, while sectors derived from it were similar in all respects to the rapid-growing wild-type T95 parent (strains 44A and C in FIG. 1D) or a moderately-slow growing yellow-brown strain with the T12 phenotype (44C in FIG. 1D). Similarly, colonies derived from single spores differed markedly; strain 44-7 was again similar to the wild-type T95 parental strain, while 44-10 and 44-11 were slow-growing strains with the T12 phenotype. All of the strains in FIGS 1C and 1D were prototrophic except strain 44-11, which required histidine for growth.

TABLE 1

Colony morphology, enzyme phenotype, and growth rate on various media of selected progeny strains resulting from fusion of auxotrophs of strains T12 and T95 of *Trichoderma harzianum*. Also presented a data on the range of single spore subprogeny that were obtained from these strains.

| Strain | Enzyme phenotype | Colony appearance | Growth on various media | | |
|---|---|---|---|---|---|
| | | | BM | BM + H | BM + L |
| T12 | T12 | green-sporulation, | F | F | F |
| T95 | T95 | light green sporulation, heavy growth | F | F | F |
| T12 his⁻ | T12 | weak sporulation moderate growth | — | M | — |
| T95 lys⁻ | T95 | weak sporulation moderate growth | — | — | M |
| 7 | T12 | like T12 | F | F | F |
| 12 | T95 | like T95 | F | F | F |
| 24 | T12 | like T12 his⁻ | — | M | — |
| 29 | T12 | like T12 his⁻ | — | M | — |
| 34 | T95 | very sparse growth little sporulation | S | S | S |
| 44A | T95 | similar to T95 | F | F | F |
| 44B | T12 | similar to T12 his⁻ | M | M | S |
| 60 | T95 | like T95 | F | F | F |
| 70 | T12 | very slow growth | S | S | — |
| 83A, B, or C | T12 | brown, wrinkled, | S | M | S |

TABLE 1-continued

Colony morphology, enzyme phenotype, and growth rate on various media of selected progeny strains resulting from fusion of auxotrophs of strains T12 and T95 of *Trichoderma harzianum*. Also presented a data on the range of single spore subprogeny that were obtained from these strains.

| 83D | T95 | very few spores (83A, C); or pinnate, sporulating (83B) like T95 | | | |
|---|---|---|---|---|---|
| | | | F | F | F |

| Strain | Growth on various media | | Single-spore sub-progeny types |
|---|---|---|---|
| | BM + HL | PDA + HLB | |
| T12 | F | — | all like original |
| T95 | F | F | all like original |
| T12 his⁻ | M | — | all like original |
| T95 lys⁻ | M | M | all like original |
| 7 | F | — | all like strain 7 |
| 12 | F | F | mixture of types; some like T95 lys, and others like T95 |
| 24 | M | — | variety of types; including ones like T95, nearly asporulant strains (FIG. 2) with weak protroghy, ad others like T12 his⁻ |
| 29 | M | — | variety of types; including stellate growth patterns (FIG. 2) |
| 34 | S | S | all like strain 34 |
| 44A | F | F | all like T95 |
| 44B | M | — | Two types of colonies one type was rapid-growing, prototrophic, the other grew more and required lysine |
| 60 | F | F | Two types of colonies. approximately ½ like T95 and ½ like T12 |
| 70 | S | — | all like strain 70 |
| 83A, B, or C T12 | M | — | all like strain 83A, B, or C |
| 83D | F | F | all like strain 83D |

*Abbreviations for media are BM, basal medium; BM + H, basal medium + histidine; BM + L, basal medium + lysine; BM + HL, basal medium + histidine and lysine; PDA + HLB, potato dextros agar + histidine, lysine, and benomyl. Abbreviations for growth rate are f, fast (35 mm diameter colonies in petri dishes after 3 days growth at 25° C.; m. medium (15-35 mm growth), S, 2-15 mm growth in three days, and —, no growth.

High yields of nearly pure protoplasts can be obtained either from young thalli or germlings of *T. harzianum* strains T12 or T95, using a procedure similar to that used by Grachek, 1984, supra. Various enzyme preparations were used with immature or mature conidia, but none gave more than about 50% protoplasts. These results are at variance with those of Toyama et al., 1984, supra, but he used other strains and enzyme preparations. About 10% of the protoplasts from young germlings or thalli gave rise to colonies on PRM. In other systems, regeneration frequencies ranged from 1 to 50% in filamentous fungi, while regeneration of protoplasts from yeasts may approach 100% (Picataggio et al., 1985, supra: Peberdy, 1979, *Ann. Rev. Microbiol.* 33:21-39).

The procedure for protoplasts fusion with PEG gave high levels of fusion; with the T95 his⁻ ×T95 lys⁻ cross, about 10% of the regenerating thalli were protrotrophic. All of the numerous prototrophic thalli from the cross between the two auxotrophs of T95 appeared to be stable heterokaryons. Colonies derived from single conidia of prototrophic progeny were auxotrophic for either histidine or lysine in approximately equal numbers. These data indicate that the two nuclear types were present in approximately equal numbers.

Conidia of *T. harzianum* are multinucleate, unlike the condition reported by Toyama et al., 1984, supra for *T. reesei*. There is, therefore, no advantage to preparing protoplasts from conidia; in our studies protoplasts derived from any source contain 2-12 nuclei.

Conidia are, however, apparently genetically homogenous, probably because all of the nuclei in a conidium are derived from a single nucleus (Picataggio et al., 1984, supra). Evidence for this was provided by the consistent isolation only of auxotrophs from prototrophic strains derived from fusion of T95 lys⁻ and T95 his⁻. If nuclei in conidia were derived from two or more nuclei from the thallus, prototrophic progeny should have been isolated. The very low (1 in $10^5$) rate of isolation of prototrophic strains from conidial suspensions may have resulted from a rare bit of heterokaryotic hyphae in the suspension, or from a rare heterokaryotic conidium. They do not represent stable diploids, since a second generation of conidial suspensions obtained from prototrophs derived from single conidial suspensions again gave rise primarily to auxotrophic strains, with again only a very low level of prototrophic colonies. These results are similar to those of Picataggio et al., 1984, supra with *T. reesei*, and are at variance with those of Toyama et al., 1984, supra with the same species.

Events following fusion of T12 his⁻ and T95 lys⁻ followed a very different pattern. Fusion mixes with both crosses were similar in appearance. However, while regeneration of fused protoplasts of the two auxotrophs of T95 gave rise to numerous prototrophic thalli within 48 hours, fusion products of the T95×T12 cross grew very slowly. Isozymic analysis the immediate progeny of the T12×T95 fusion showed only the pattern of T12 in >99% of the strains. These strains also grew faster on media containing histidine than on media not containing this amino acid, and were susceptible to benomyl, all of which are characteristic of T12.

However, with increasing time of culture, more rapidly growing sectors frequently appeared. These were of both the T95 and the T12 type, indicating that both nuclear types were present in the original thallus, even though the T95 phenotype could not be detected. The weakly prototrophic nature of the original thalli from this fusion suggests that the T95 genome was present and providing a low level of nuclear complementation. Nonexpression of one parental genome has been noted in fusion products of *Bacillus subtilus;* with this bacterium colonies were obtained which readily switched from expression the genome of one parent to the genome of the second parent, indicating complete repression of one genome in the presence of the other (Hotchkiss and Gabor, 1980, *Proc Natl. Acad. Sci.* 77:3553-3557).

The results were corroborated by the behavior of single conidial strains. Some of these were of the rapid-growing T95 phenotype even though the original progeny strains were slow-growing and of T12 phenotype. Conidia giving rise to the T95 isozyme phenotype were rare. The age of the strain (reflecting time for genetic segregation) may affect whether conidial strains will all be alike or different. Most of the progeny strains exhibiting diversity among single spores isolates (e.g. strains 24 and 29) were from the second cross, and so had been maintained only for about 4 months prior to conidial plating, while strains with no diversity (e.g. 7, 12, 34, 44A, 44B, 70, and 83A, B, C, or D) were all from the first cross, and had been maintained for 10 months prior to conidial isolation. Strain 60 however, was from the first cross and contained a range of genetic types in conidial isolations.

Some progeny strains were very different from the parental strains, and maintained this nonparental character upon single spore isolation. Strain 83A, B, or C for example, had an enzyme phenotype like T12, but differed in hyphal color (brown vs. hyaline), growth type (restricted, wrinkled vs spreading, smooth), and sporulation ability (very sparse vs abundant) relative to the parental strains (FIG. 1A). Strain 34, conversely, grew very sparsely, and sporulates infrequently and has a enzyme genotype like that of T95. All conidial sub-progeny of strains 83A, B, C, or D, or 34 were protrophic, and maintained all morphological and isozyme characters of the original progeny strain through conidiation. Strains 22 and 7 grow more rapidly than either the auxotrophic or wild-type parental strains. These data suggest that these some progeny are significantly different genetically from either parent.

Moreover, strains such as S24, 29, and the original strain 44, gave a variety of colony types when single conidia were isolated. These data indicate that there are a range of nuclear types in the original thallus, including ones similar to the parental strains and others that are significantly different.

EXAMPLE 2

The purpose of this Example is to describe the preparation and properties of several superior biocontrol strains of *Trichoderma harzianum*.

Media. Several media were used. These included the basic medium (BM) of Toyama, 1984, which contained 1.4 g/l $(NH_4)_2SO_4$, 30 mg/l urea, 2 g/l $KH_2PO_4$, 20 g glucose, 30 mg/l $MgSO_4$, 5 mg/l $FeSO_4\ 7H_2O$, 1.4 mg/l $ZnSO_4\ 7H_2O$, 1.6 mg/l $MnSO_4\ H_2O$, 2 mg/l $CoCl\ H_2O$, and 20 g agar. All components except the agar were dissolved water at a 2× concentration, and filter-sterilized by passage through a 0.45 μm filter. The agar was sterilized by autoclaving the two components. They were then brought to 60° C., mixed, and poured into petri dishes. Addition of 10% w/v sucrose as an osmiticant resulted in protoplast regeneration medium (PRM). The media amended with either 150 μg/ml histidine, 150 μg/ml leucine, or the combination, and were designated as BM+L, BM+H, BM+HL, or PRM+L, PRM+H, or PRM+HL for the basal or the protoplast regeneration medium plus these amino acids, respectively.

In addition, Difco potato dextrose agar or both (PDA or PDB, respectively) was used, as well as PDA amended with amino acids and/or 10 g/ml benomyl, to give PDA+H, PDA+L, PDA+HL, or PDA+HLB. Benomyl was suspended in 10 ml sterile water and added prior to sterile medium cooled to 60° C., and then poured into petri dishes.

Strains used. Parental strains of *Trichoderma harzianum* Rifai were T95 (Ahmad and Baker, 1987, supra: American Type Culture Collection [ATCC] 60850) and T12 m (Hadar et al, 1984, supra: ATCC 20737). T95 was a mutant resistant to benomyl at 50 μg/ml, while growth of T12 was prevented by 3 μg/ml benomyl. Auxotrophic mutants requiring lysine or histidine (T95) or histidine (T12) were prepared by irradiating conidia with ultraviolet irradiation from a 15 watt germicidal florescent lamp until ca. 99% of the conidia were killed. Irradiated conidia were transferred to a broth prepared from BM, but without agar. This mixture was incubated with shaking at 25° C. for 1 week, and was filtered daily through four layers of sterile cheesecloth to remove protorophic conidia. The nongerminated conidia were plated on BM+HL containing 0.1% w/v Igepal Co630 as a colony restrictor (Norton and Harman, 1985, supra), and incubated at 25° C. until colonies developed. These colonies were then individually transferred back to BM, and colonies that did not grow on this medium tentatively was considered to be auxotrophs. Identity of auxotrophs were confirmed by inability to grow on BM, but ability to grow on BM+H or BM+L. Once auxotrophs were found, they were single-spored to obtain homogenous and stable auxotrophs. Only auxotrophs that gave no growth upon repeated transfers to BM from actively growing colonies BM+H or BM+L were used further. Plating of conidia from auxotrophs gave reversion frequencies of one in $10^{10}$ or less. Colonies with a requirement for lysine are indicated by lys⁻, for histidine by his⁻, and benomyl resistance is indicated by ben⁺.

Isozyme analysis. Additional genetic markers were identified by subjecting extracts of horizontal starch gel electrophoresis followed by specific enzyme stains. For this purpose, cultures were grown in 10 ml of PDB in 25 ml flasks for 3-5 days at 25° C. on a reciprocating shaker. Resulting thalli (appx. 50 mg dry weight) were removed from flasks, dried briefly on filter paper, and placed in about 0.2 ml ice-cold extraction buffer (0.05M tris (hydroxymethyl) aminomethane—HCl pH 7.1). Two gel buffer systems were used for the analysis, these were the histidine gel system at pH 6.5 described by Cardy et al., 1972, supra and the tris citrate/lithium borate system of Selander et al., supra. The procedure for electrophoretic analysis of the extracts was described by Weeden, 1984, supra. Strains T12 and T95 were screened for reproducible differences in isozymic mobility on about 70 enzyme systems, using the procedures described by Weeden (1984). Of these, four were found to give reproducible and easily-distinguished differences between strains T95 and T12. These enzymes were fumarase (FUM, E.C. 4.2.1.2.), phosphoglucomutase (PGM, E.C. 2.75.1) α-D-glucosidase (GLU, E.C. 3.2.1.20), and triosephosphate isomerase (TPI. E.C. 5.3.1.1). The histidine gel system was used for FUM, PGM, and GLU, while the tris-citrate/lithium borate system was used with TPI. Visualization of enzyme activity was accomplished using the assay systems described by Weeden and Gottlieb, 1980, supra for PGM and TPI, and by Brewer, 1970, supra for FUM. A modification of the assay described by Smith, 1976, supra that contained 0.1M tris-HCl pH 7.1 and 3 mM 4-methylumbelliferyl α-D-glucoside was used for GLU.

Protoplast isolation. Appx. 100 small squares (2–4 mm$^2$) from young, nonsporulating colonies on PDA were transferred to 200 ml of PDB amended with 1.5% yeast extract and incubated overnight with shaking at 25° C. to give spherical thalli each about 4–6 mm in diameter. These were collected on Miracloth and incubated 24 hours in 80 ml of a 13 mg/ml solution of Novo-Zym 234 (Novo Laboratories, Wilton, Conn.) in 0.7M NaCl. Protoplast enzyme mixtures were filtered aseptically through four layers of cheesecloth to remove hyphae and other debris, and protoplasts were harvested by centrifugation at 100 ng for 5 min.

Protoplast Fusion. Protoplasts were fused using a procedure similar to that described by Turgeon et al., 1985, supra. One ml of a suspension containing about 10$^8$ protoplasts in STC were prepared with about that contained equal numbers of protoplasts from each parental strain. To this was added 200 μl of solution containing 60% (w/v) polyethylene glycol (PEG) solution (appx. molecular weight 3350, Sigma Chemical Co., St. Louis, Mo.), 10 mM CaCl$_2$, and 10 mM tris-HCl, pH 7.5 The PEG was mixed with the protoplast suspension by gently rolling the tube. A second 500 μl aliquot of the PEG solution was added, the mixture again gently mixed, and finally a third 500 μl aliquot was added and mixed by rolling. Following incubation at 30° C. for 10 minutes, the mixture was then diluted with 1.1 ml of STC, the mixture mixed gently. This dilution step was repeated, and finally 2.2 ml of STC were added. After fusion and dilution, protoplasts were recovered by centrifugation and resuspended in 5 ml STC.

Test of Biological Properties. Selected strains were tested for their biocontrol capability, and for their rhizosphere competence. All tests utilized cucumber (*Cucumis sativus* L) 'Slicemaster' seeds.

Tests of biocontrol capability were conducted by planting treated seeds in Pythium - infested soil. Solid matrix priming (SMP) seed treatments are described hereinabove and elsewhere (Harman and Taylor *Phytopathology*, 78:520–525,(1988). In addition, seeds were also treated using a conventional method slurry technique (Hadar et al., 1984, supra). Tests for biocontrol capability were performed with both SMP and slurry-treated seeds (Harman and Taylor, 1988, supra).

Rhizosphere competence was determined by a modification of the method of Chao et al., 1986, supra. Split plastic pipes 22 mm in diameter and 14 cm long were taped together to form a tube, and stoppered on one end with cotton. Noninfested Arkport sandy loam at −7 mPa$_2$ was used to fill the tubes, and was compacted to give a bulk density of about 1.1. One treated seed was planted in each tube, and these were then placed in a humid chamber that maintained 100% relative humidity. After incubation for 4 days, tape was removed from the tubes, the two halves separated to expose the undisturbed soil core, and the seedling lifted from the soil. Roots were gently tapped to remove loosely-adhering soil, and the roots were cut into 1 cm sections. These were placed on plates containing a Trichoderma-selective medium (Harman and Taylor, 1988, supra) and incubated for 3 days.

RESULTS

Progeny from crosses between T12 and T95 initially grew very slowly, and are described in Example 1. More rapid-growing sectors arose, and these could be divided into several classes. Those growing very slowly were not tested since good growth and proliferation are required for biological control.

Strains tested for biocontrol activity were either with isozyme phenotypes identical to the T95 parent and with rapid growth; with isozyme phenotypes identical to the T12 parent, moderate growth, and antibiotic production; or with isozyme phenotypes like the T12 parent and with very rapid growth. In preliminary tests, only the latter types gave improved biocontrol capability, and three were tested more extensively. These are designated strains 1295.7 (ATCC 20846), 1295-22 (ATCC 20847), and 1295-74 (ATCC 20848).

Figure 2B:
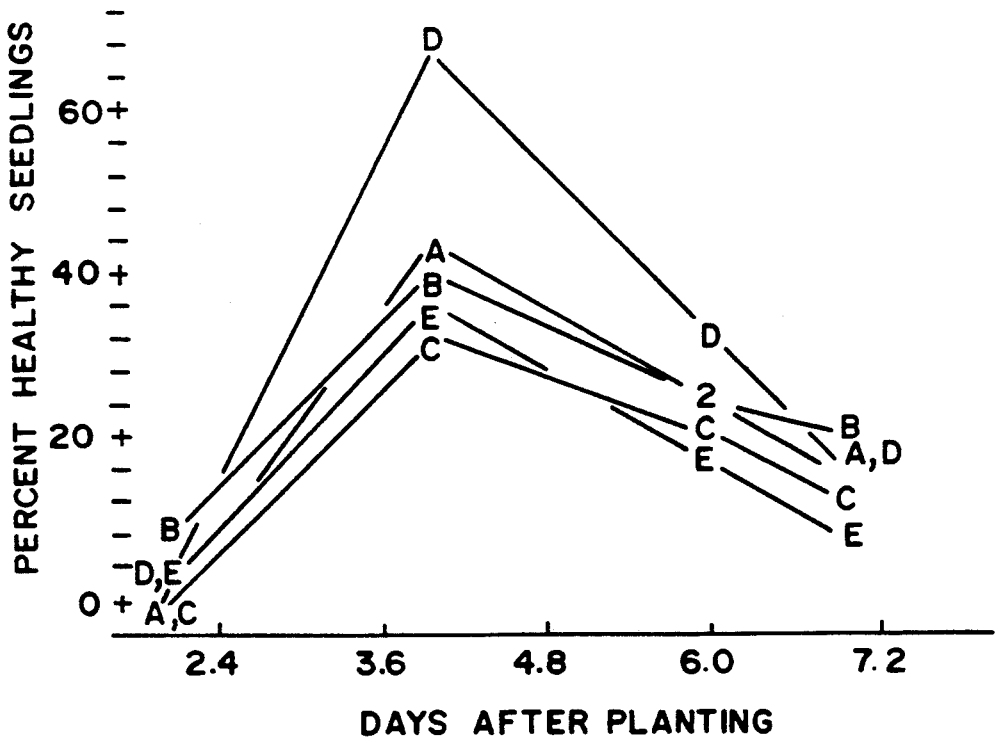
In FIG. 2B, differences at days 2, 6, and 7 are nonsignificant, and the minimum significant difference at day 4=17%.

When applied to cucumber seeds and planted in infested soil, the results shown in FIG. 2 were obtained. When added only in a Methocel slurry, the three progeny strains and the parental T12 and T95 strains are performed similarly. However, strain 1295-22 gave significantly more total seedlings than treatment with any other strain. By 7 days after planting, however, only 6–18% of seedlings survived subsequent attack by Pythium (FIG. 2B).

When these strains were applied in SMP, the progeny strains performed markedly better than the parental strains. Initial stands 3 days after planting were similar with all treatments. Subsequently, however, post-emergence damping off occurred in the seedlings treated with the parental strains, but not with the progeny. Eighty-six to 96% of the seedlings arising from progeny-treated strains survived to the end of the experiment (8 days), while only 64 to 26% of seedlings arising from T12 and T95, respectively, survived to the end of the experiment (FIG. 2A).

Moreover, the seedlings that did survive differed markedly in appearance. Those arising from seeds treated with SMP or alone or with SMP+T12 or T95 had cupped petioles, and appeared unhealthy, while those arising from seeds treated with SMP+any of the progeny strains were vigorous and had normal cotyledons. When removed from soil, the abnormal-appearing seedlings were found to have reduced root systems with browning. Conversely, root systems from the normal-appearing seedlings arising from SMP+progeny-treated seeds were larger and whiter. The reduced root systems with browning are symptomatic of attack by Pythium spp.

When rhizosphere competence was measured, parental and most progeny strains colonized similar number of root sections. Thus, 50, 63, 54, and 59% of root sections were colonized by strains T12, T95, 1295-7, and 1295-74. However, strain 1295-22 colonized 84% of root sections, and appears to possess superior rhizosphere competence.

These results demonstrate that, particularly when applied in SMP, strains 1295-7, 1295-22, and 1295-74 provide nearly perfect stands of cucumbers in Pythium-infected soil. Additionally, SMP+these progeny strains provide excellent protection against damping-off. This is particularly remarkable when the fact that numbers of Pythium propagules are such that 0% stands are obtained with non-treated seeds, and that protection provided by SMP+parental strains is superior to that provided by the fungicide thiram, with or without SMP.

Moreover, these progeny strains+SMP provide excellent protection against seedling disease. This is shown both by the lack of post-emergence damping off, and by the lack of root disease 8 days after planting.

Results with conventional slurry treatment with a Methocel sticker provided fewer differences. This lack of difference may result from the fact that Pythium spp attack seeds very rapidly (Harman and Hadar, 1983, supra), and may infect seeds more rapidly than Trichoderma spores applied in a Methocel slurry can germinate. Thus, many seeds may become irreversably infected before even the best Trichoderma strains become active. When seeds are given SMP, however, Trichoderma spores can germinate and become active before they are planted. Thus superior biocontrol agents may be more easily identified by their superior results with SMP than with a conventional slurry treatment.

Finally, strain 1295-22 appears to be highly rhizosphere competent. The ability of a biocontrol agent to colonize root surfaces permits it to be in the best position to protect roots against attack by soil-borne fungi, and is a valuable attribute.

EXAMPLE 3

In this example, the parental strains of *T. harzianum* (T12 and T95) were compared with two progeny strains (1295-22 and 1295-106 prepared through protoplast fusion) in the presence or absence of solid matrix priming. For comparison, seeds were treated only with the Pelgel sticker used in all other treatments, or with a standard fungicide, usually thiram, again in the presence or absence of solid matrix priming. In seedling assays conducted in growth chamber experiments, seeds of cotton, cucumber, pea, snapbean, sweet corn and wheat were planted in soil infested with *Pythium ultimum;* wheat in soil containing *Fusarium graminearum,* cucumber and snap bean in soil containing *Sclerotium rolfsii;* and radish and cucumber in soil infested with *R. solani.* With all crop pathogen combinations, Trichoderma strains increased stands relative to the non-treated control, and were as effective as the standard chemical fungicides, even in the absence of solid matrix priming. Priming increased stands of seeds treated with Trichoderma strains in soils infested with *Fusarium graminearum* and *Pythium ultimum* but not in soils infested with *Rhizoctonia solani* or *Sclerotium rolfsii.* In soils infested with *P. ultimum,* strain T95 generally gave the poorest results, T12 was intermediate, while the progeny strains (1295-22 and 106) gave improved stands; with the other pathogens, strains gave similar levels of protection. In trials with cucumber in Pythium infested soils, seedlings from seeds treated with 1295-22 or 106 were more robust than those treated with other Trichoderma strains; those differences were related to greater root volume of seedlings. Root volumes of plants grown from seeds treated with 1295-22 or 106 were 41 or 21% respectively, greater than those from plants treated with T12. Field trials were conducted. Stands of peas in two trials were not significantly enhanced by treatment with Trichoderma strains in the absence of priming, but were improved by priming+-Trichoderma strains. Roots of peas were also sampled at plant maturity to determine the amount of root colonization by the Trichoderma strains. The protoplast progeny strains were more effective than the parental strains; ≧95% of root segments were colonized by 1295-22 or 106, while 31-67% were colonized by T12 or T95. Field trials also were conducted with sweet corn, using strain T12 only (required EPA permission to conduct field trials with protoplast fusion progeny was not obtained for this crop). Across two trials, this strain increased plant stand, reduced seedling mortality, and increased plant growth relative to no treatment. The increased plant growth was evident for the entire duration (98 d) of the longest trial.

MATERIALS AND METHODS

Strains. The strains tested were either the parents or the progeny from a single fusion. The parental strains were *Trichoderma harzianum* Rifai, strain T12 (ATCC 56678) (American Type Culture Collection [ATCC] and *T. harzianum* strain T95 (ATCC 60850)). Strain T12 was chosen because it is known to possess good biocontrol ability against Pythium and Alternaria spp., as well as ability to compete well with other microflora [Harman et al., *Phytopathology.* 74:106-110 (1984); Hubbard et al, *Phytopathology.* 72:655-659; Taylor et al, *Sci. Hort.* (In press) (1988)]. Strain T95 also possesses good activity against Pythium spp. and is rhizosphere competent (Ahmed et al, *Phytopathology,* 77:358-362 (1987).

Details of preparation, fusion of protoplasts, and of the genetic nature of progeny obtained are described elsewhere [Stasz et al., *Mycologia,* 80:141-150 (1988)]. Briefly, complementary auxotrophs of the two strains were prepared, protoplasts were produced from these and fused in the presence of polyethylene glycol. Fusion mixtures were plated on a glucose-nutrient salts medium, and prototrophic colonies collected. The resulting progeny initially grew very slowly, and were weakly prototrophic. They were unstable, and numerous more rapidly growing sectors appeared. These varied markedly in morphology, but were similar to one or the other parents in isozyme patterns. Progeny strains with various morphotypes and isozyme patterns were tested as cucumber seed protectants against Pythium spp, using the procedures described below. Most were much poorer bioprotectants than the parental strains, but one class of progeny was superior. Several strains were tested more extensively and two were selected for the work described in this Example. These were designated strain 1295-22 (ATCC 20847) and 1295-106 (ATCC 20873).

These strains were fully prototrophic and identical to strain T12 in isozyme pattern. They grew more rapidly than either parental strain, on potato dextrose agar, the growth rates at 24° C. were 17, 20, 22 and 23 mm/day for strains T95, T12, 1296-22 and 1295-106, respectively, while at 11° C., growth rates were 3.1, 6.2, 6.7 and 6.5 mm/day for these same strains. None grew at 7° C. Although strains 1295-22 and 1295-106 are isozymically identical to strain T12, the parental and progeny strains can readily be distinguished by their appearance on potato dextrose agar amended with 75 ug/ml cycloheximide, 20 ug/ml nystatin, 100 ug/ml streptomycin sulfate, 100 ug/ml chlortetracycline and 1 mg/l Igepal C0630 (Applied Science Labs, Deerfield, Ill.) (Chao et al, *Phytopathology*, 76:60-65 (1986)). On this medium strain T12 initially forms a tan colony with brown pigment in the medium. Blue spore masses are produced with little diurnal variation. The progeny strains initially form whitish colonies with little diffusable pigment. Spore masses are green and diurnal zones of heavy sporulation are produced.

Crops and Pathogens. Crops tested were cucumber (*Cucumis sativus* L. cv. 'Slicemaster'), wheat (*Triticum aestivum* L. cv. 'Houser'), sweet corn with the su gene and the sh-2 gene (*Zea mays* L. cvs. 'Jubilee' and 'Florida Stayswet', respectively), radish (*Raphanus sativus* L. cv. 'Early Scarlet Globe'), snap bean (*Phaseolus vulgaris* L. cv. 'Bush Blue Lake 47'), pea (*Pisum sativum* L. cv. 'Venus') and cotton (*Gossypium* spp. cv. 'Acala SJ-2' and 'Stoneville 112'). Pathogens tested were *Pythium ultimum* Trow, *Rhizoctonia solani* Kuhn, *Fusarium graminearum* Schawbe and *Sclerotium rolfsii* Sacc.

Seed Treatments. In all cases, conidiospores were scraped from cultures grown in petri plates on potato dextrose agar. These were suspended in a 10% w/v aqueous suspension of Pelgel (Nitragin Corp., Milwaukee, Wis.) at $10^7$-$10^8$ conidia/ml (8). These spore suspensions were used to treat seeds to give full coverage of the seed surfaces. For wheat, radish and cucumber, 1 ml of suspension was used to treat 4 g of seeds; for Jubilee sweet corn, 1 ml was used to treat 10 g of seeds; for Florida Staysweet corn and Venus peas 1 ml treated 6 g of seeds; and 1 ml of suspension was used to treat 7.8 g of cotton seeds. For comparison, seeds were treated with Pelgel alone, or with fungicides. For wheat, Vitavax 200 (17% carboxin and 17% thiram) was used at the rate of 420 ug active ingredient of each component per g of seeds. For all other crops, thiram alone was used. For cucumbers, cotton and radish, this fungicide was added at the rate of 1.35 mg/a.i. per g seed, while for all other crops 700 ug/g seeds was used. These rates are those recommended on the label for those fungicides on each seed kind.

Solid matrix priming was performed as described above. Seeds treated as described above were mixed with 1.5 parts by weight of a finely ground Leonardite shale (Agro-Lig. Arlington Heights, Ill.) for all crops except peas and bean, while for these seeds two parts of Agro-Lig were used. Sufficient water was added to be just below the threshold required for seed sprouting. For each seed kind, percent moisture contents were as follows (based on the dry weight of Agro-Lig): cucumber, 60%; sweet corn, 60%; wheat, 55%; radish, 60%; snap bean, 75%; cotton, 75%; and pea, 80%. Seeds of all crops except cotton were then incubated for 4 days at 20° C.; cotton was incubated at 25° C. to avoid chilling damage. With cotton, this incubation regime permitted a great deal of saprophytic microbial growth, so experiments were conducted to determine whether moisture content or incubation time could be reduced to alleviate this problem. We found that incubation time could be reduced to one day with no adverse effects on biocontrol ability; data on Acala SJ-2 was with 4 d incubation, while data on stonevelle 112 was with 1 d incubation. After incubation, excess Agro-Lig was removed from all seed kinds by sieving and seeds were planted.

Seedling assays. Seeds treated as described above were planted in 300 g Arkport sandy loam soil contained in 10×10×5 cm plastic boxes. Five boxes were planted of each treatment and each box was considered a replicate. For radishes, 30 seeds were planted per box; for cucumber, ten seeds were planted, for cotton and wheat, eight were planted, while for pea and snap bean each box received five seeds. Soils were adjusted to a moisture potential of −70 kPa at the beginning of each experiment. Boxes containing seedling assays were placed in larger clear plastic boxes with lids which obviated the need for irrigation over the 7-14 day experimental period. Experiments were conducted at 22°-27° C. with a 12 hr photoperiod provided by cool white fluorescent lights.

In all experiments, soils were infested with one of the pathogenic fungi listed earlier. For *Rhizoctonia solani*. *Sclerotium rolfsii* and *Fusarium graminearum*, fungi were grown on an autoclaved mixture of 20 g wheat and 30 ml water contained in petri dishes. When this substrate was completely colonized (i.e. the entire contents of the plate fused into a single mass with hyphae) the petri dish lids were removed and the cultures dried in a sterile air stream provided from a laminar flow transfer hood. The dried mixture was ground in a Waring blender and kept at 4° C. until use. Preliminary experiments were conducted to determine minimum levels of each pathogen that permitted no (or very little) seedling survival for 8 days. For *R. solani*, this level was 50 ug autoclaved wheat preparation / g soil; for *S. rolfsii* it was 300 ug/g and for *F. graminearum* the level was 16,000 ug/g.

Field trials with peas. Several trials were conducted with peas in the summer of 1987. The first trial was planted on Apr. 23, the second was planted on May 29. Soil temperatures in the first trial were cold, with daily low temperatures frequently at 7° C. or less. Soil temperatures in the second trial were warmer, not dropping below 20° C. Trials were planted in a Lima silt loam. At both dates, two separate trials were conducted. In one, seeds were not treated, treated with metalaxyl at the rate of 30 ug/g seeds, with strain T12, T95, 1295-22, or 1295-106. With all seeds Pelgel was used as a sticker. All treatments were done with and without priming. Fifty seeds of each treatment were planted in rows 4m long with 0.45 m between rows. Five rows (replications) were planted per treatment, and the entire plot was arranged in a randomized complete block design. These trials are hereafter designated row trials. In addition to these trials, at each date were planted nontreated seeds, seeds treated with metalaxyl without priming, with metalaxyl with priming, T12 with priming, 1295-22 with priming, or 1295-106 with priming. One hundred seeds were planted in 1×1m plots to simulate commercial plant spacing. Each plot was separated from its neighbor by 0.3m. These plots are hereafter designated block plots.

*Pythium ultimum* was added to row trials to augment that occuring naturally in the soil. The organism was fragmented in a Waring blender, and diluted in water. This mixture was applied at planting. A tractor mounted system delivered the additional inoculum directly into the seed furrow immediately after the seeds were sown. The inoculum at $3 \times 10^5$ sporangia/row was placed directly onto the planted seed. The soil in the planting furrow was sampled after seedlings emerged, and the Pythium numbers as determined by plating on a selective medium were 400-500 colony-forming units/g of soil.

In addition to row and block trials, trials were conducted specifically to measure the ability of various strains to colonize root surfaces. Fifty pea seeds each were treated with strains T12, T95, 1295-22, or 1295-106 in the presence and in the absence of priming. Plants were separated from ones grown from dissimilarly treated seeds by a distance of at least 5m. These were planted in a Lima silt loam, and plants allowed to grow until they were at the mid-bloom stage. Five plants produced from each seed treatment were carefully dug and the soil washed from the roots. One cm segments were taken from each root system at the cotyledonary attachment, at the middle and at the tip of the tap root. Lateral roots were similarly sampled at the midway point and at the root tip. All lateral roots were sampled, so 18-20 samples were taken from each root segment.

Segments were plated on a medium highly selective for Trichoderma spp. Colonies developing on the selective medium were transferred to CCNSI for T12, 1295-22, or 1295-106, where strains were easily distinguished based on their morphology. Colonies derived from roots grown from seeds treated with T95 were plated on potato dextrose agar amended with 40 ug g benomyl (PDA+B). Identity of colonies that developed on CCNSI or PDA+B, was spot checked using isozyme electrophoresis. Strains of Trichoderma can be readily distinguished using this technique.

RESULTS

Figure 3:
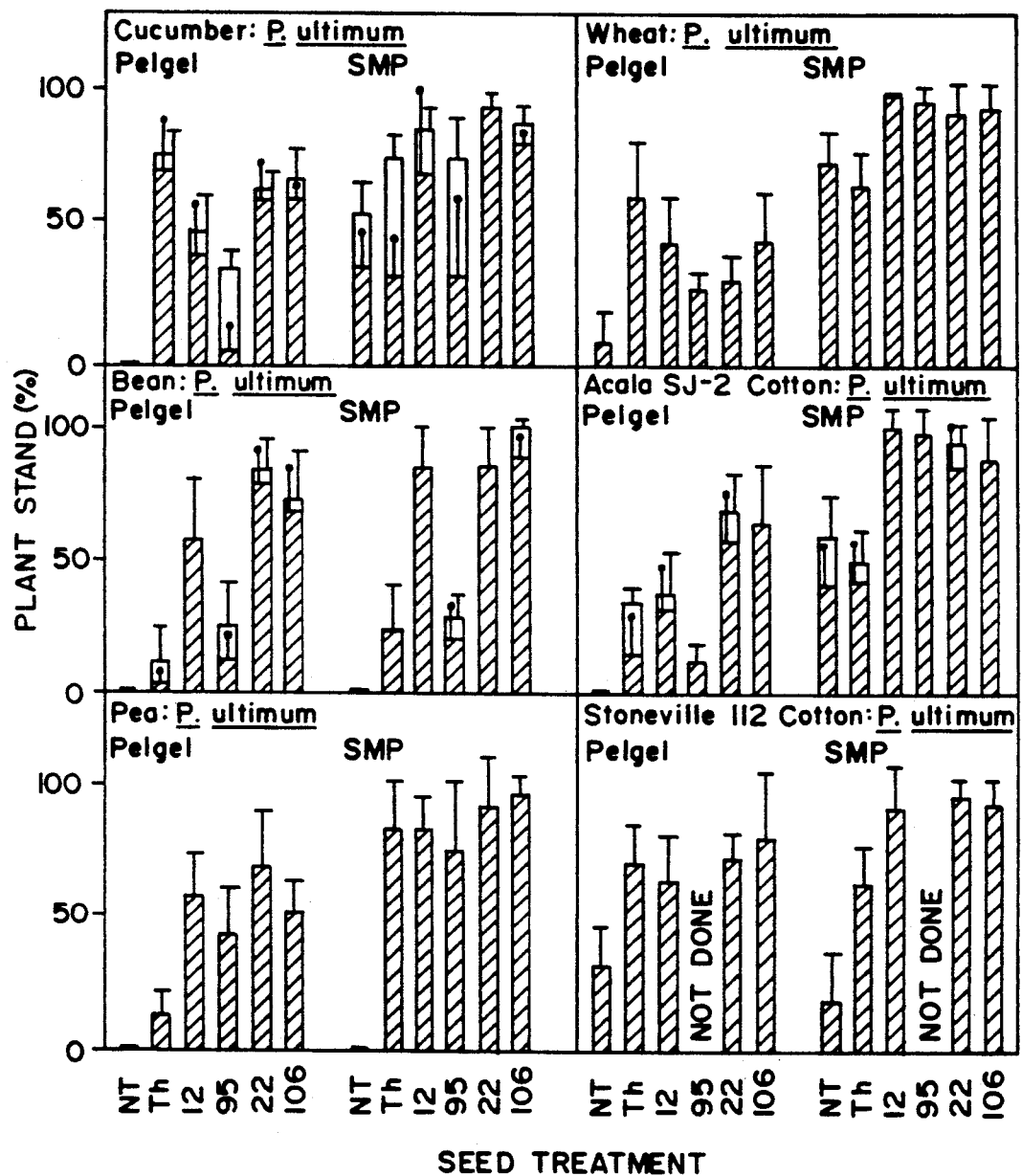
FIG. 3, graphically presents maximum and final stands of various crops from seeds treated with nothing (Pelgel sticker only), thiram (abbreviated th in figure legend) (wheat was treated with Vitavax), or *Trichoderma harzianum* strains T12, T95, 1295-22, or 1295-106 in the absence or in the presence of solid matrix priming (SMP). Seeds were planted in soil infested with *Pythium ultimum*. The difference between the maximum and final stands equals the amount of post-emergence damping off. The bars represent the standard deviations of the maximum and final stands.

Seedling assays with *P. ultimum*. With all crops, the biocontrol strains and the chemical fungicides provided significant protection against *P. ultimum*. With most crops except snap bean, more seedlings emerged and survived from primed seeds than from non-primed seeds (FIG. 3). While results with most seed treatments gave consistent results among experiments, priming alone gave highly variable results. For example, with cucumber, maximum stands ranged from approximately 3 to 60% (data not shown).

Differences among strains were apparent. In general, strain T95 was the least effective of those tested. With most crops, strains T12, 1295-22, and 1295-106 gave equivalent levels of protection. However, in a few cases the latter two strains gave better results than T12. In cucumber with SMP, considerably less post-emergence damping-off occurred with 1295-22 or 1295-106 than with any other treatment. In the absence of SMP, stands of cucumbers, both cultivars of cotton, and beans were 15-20% greater with the protoplast fusion progeny than with strain T12. With wheat, stands from T12 treated seeds were greater than those from seeds treated with 1295-22 (FIG. 3).

In all cases, without priming the Trichoderma strains were at least equivalent to the standard fungicides. The best results in all crops except sweet corn were obtained with priming plus Trichoderma strains T12, 1295-22, or 1295-106. In these crops, stands went from nearly 0 with nontreated to ≧80% with these Trichoderma strains with seed priming (FIG. 3).

Figure 4:
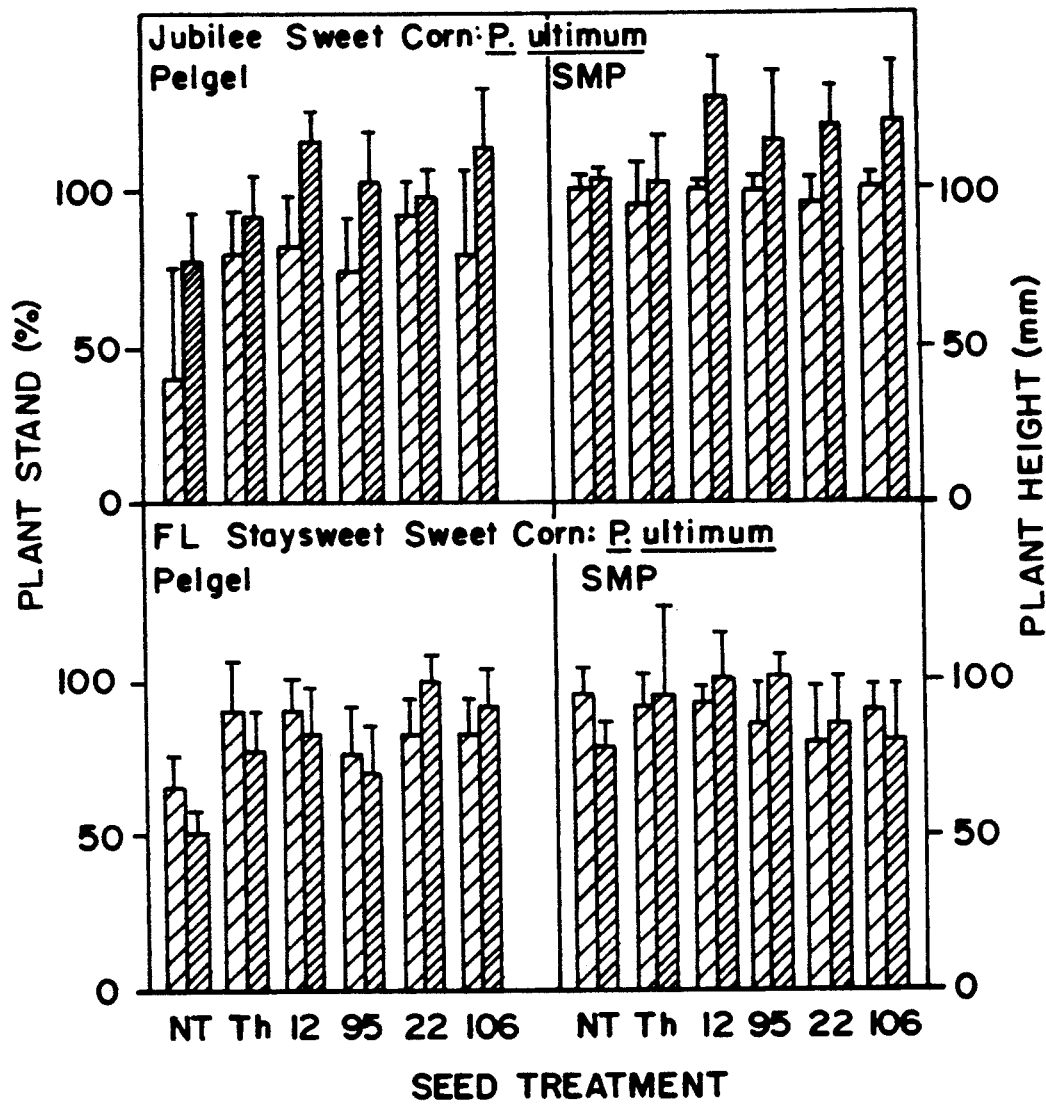
FIG 4 graphically presents stands and plant heights of Jubilee or Fla. Staysweet sweet corn from seeds treated with nothing (Pelgel sticker only), thiram (abbreviated Th in figure legend), or *Trichoderma harzianum* strains T12, T95, 1295-22, or 1295-106 in the absence or in the presence of solid matrix priming (SMP). Seeds were planted in soil infested with *Pythium ultimum*. The difference between the maximum and final stands equals the amount of post-emergence damping off. The bars represent the standard deviations.

Results with sweet corn differed from that with other crops. *P. ultimum* gave lower levels of seed rot than with other crops. Moreover, in only this crop, marked differences in plant height (and general plant robustness) were noted. The smallest plants were produced from non-treated seeds. Seed treatment with thiram or priming alone increased both plant stands and plant heights. With Jubilee, the best plant performance (stands and plant heights considered together) were obtained with priming plus Trichoderma strains. With Florida Staysweet, similar improved stands and plant heights were obtained with thiram, T12, 129-22, or 1295-106 in either the presence or absence of SMP (FIG. 4).

Figure 5A:
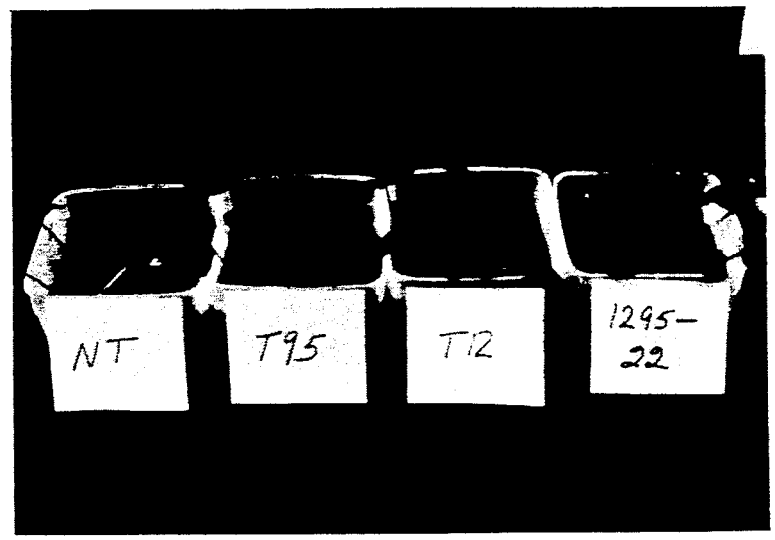
FIG. 5A and FIG. 5B.
Figure 5B:
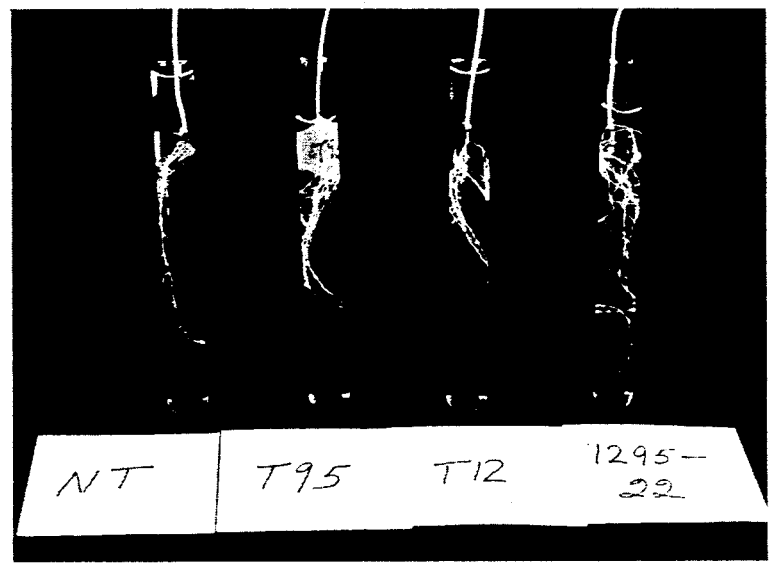

Differences in plant growth also were noted with cucumber in soil infested with Pythium. Seeds planted in soils with high seed rot potential produced seedlings that varied in appearance (FIG. 5A). Most of the seedlings succumbed to damping off with many of the treatments, but with strains T12, T95 and the protoplast fusion progeny with SMP, many survived. The seedlings from the T12 or T95— treated seeds were less vigorous, with cupped cotyledons, while those from seeds treated with 1295-22 or 106 were normal in appearance. When removed from soil, the roots of the plants from 1295-22 or 106 were found to be larger than those from other treatments (FIG. 5B). These differences were quantified by measuring the volume of water displaced by roots. The mean root volume per plant ± the standard deviation was as follows for plants produced from various seed treatments; thiram, 106±18 ul., thiram+SMP, 216±18 ul; T12+SMP, 213±61 ul; 1295-22+SMP, 301±27 ul; and 1295-106+SMP, 257±13 ul. Thus, treatment with 1295-22 or 106 resulted in seedlings with 41 or 21% greater root volumes than a comparable treatment with T12. With other treatments, post-emergence damping off killed most seedlings.

Figure 6:
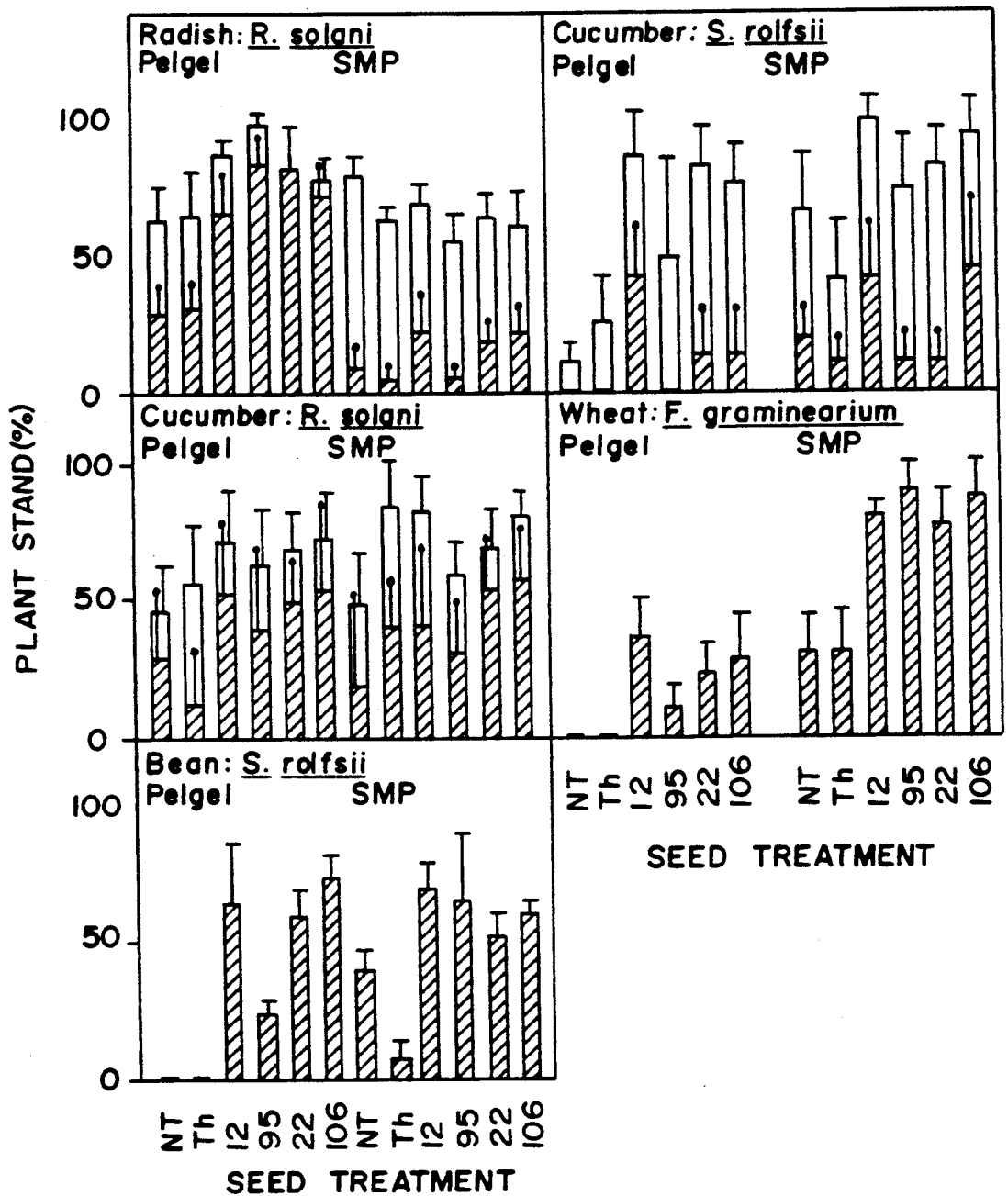
FIG. 6 graphically presents maximum and final stands of various crops from seeds treated with nothing (Pelgel sticker only), thiram (abbreviated th in figure legend), or *Trichoderma harzianum* strains T12, T95, 1295-22, or 1295-106 in the absence or in the presence of solid matrix priming (SMP). Seeds were planted in soil infested with *Rhizoctonia solani Sclerotium rolfsii.* or *Fusarium graminearum*. The difference between the maximum and final stands equals the amount of post-emergence damping off. The bars represent the standard deviations of the maximum and final stands.

Seedling assays with other pathogens. Either Trichoderma strains or chemical pesticides protected seeds of cucumber and radish from attack by *Rhizoctonia solani* and wheat seeds from *Fusarium graminearum*. Levels of protection against *R. solani* were similar with thiram or any Trichoderma strain. With priming, radish seedlings were more prone to damping off than without. A similar, but non-significant trend was observed with the cucumber *R. solani* combination (FIG. 6).

With wheat and *F. graminearum*. Trichoderma strains protected seeds better than a Vitavax seed treatment. Increases in stands were greatest when Trichoderma strains were combined with priming (FIG. 6).

When cucumber or snap bean were planted in soil infested with *S. rolfsii*, thiram was largely ineffective as a seed treatment. Trichoderma strains protected seeds and seedlings similarly, although T95 was poorer than the other strains in some trials. Priming had little effect on the efficacy of the Trichoderma against this pathogen (FIG. 3).

Pea field trials. In row trials, treatment with Trichoderma strains largely was ineffective in increasing plant stands in the absence of priming. When seed treatments with Trichoderma were combined with priming, stands were improved. Metalaxyl increased plant stands in both the presence, and absence of priming (Table 2).

There were large differences in the amount of root colonization by the various Trichoderma strains. In the block trials, accurate assessments of root colonization were not possible. Seed treatment with 1295-22 or 106 resulted in root colonization of both plots treated with these strains and also of roots of plants in adjacent plots.

In trials with wide separation between rows containing various treatments, more accurate assessments were possible. Seed treatment with either 1295-22 or 106 resulted in colonization of nearly all (≧95%) root segments from mature plants, regardless of whether or not priming was utilized. With T12 or 95, many fewer segments were colonized, and priming did have an effect (Table 2).

TABLE 2

Stands and root colonization of Venus peas in Pythium amended soils in two field trials from seeds treated with metalaxyl or strains of *Trichoderma harzianum* in the presence or absence of solid matrix priming (SMP).

| Treatment | Percent Stands Trial 1[a] | Trial 2[a] | Percent root colonization[b] |
|---|---|---|---|
| None | 52 FG | 34 E | — |
| Metalaxyl | 86 AB | 84 A | — |
| T12 | 52 FG | 44 CD | 37 |
| T95 | 50 G | 36 DE | 13 |
| 1295-22 | 57 EFG | 36 DE | 95 |
| 1295-106 | 44 G | 26 E | 97 |
| SMP | 61 DEFG | 38 DE | — |
| SMP + metalaxyl | 87 A | 88 A | — |
| SMP + T12 | 76 ABC | 68 B | 67 |
| SMP + T95 | 66 CDEF | 56 BC | 37 |
| SMP + 1295-22 | 68 CDE | 62 B | 97 |
| SMP + 1295-106 | 72 BCD | 60 B | 95 |

[a]Numbers followed by dissimilar letter are significantly different according to Waller and Duncan's BSD rule.
[b]Root colonization was determined after growing plants from seeds given the treatment indicated until they reached the sidbloom stage. Five plants of each treatment were then dug, the roots were washed, and 1 cm segments of the tap root was taken just below the cotyledonary attachment, midway down the tap root, and at the tip of the tap root. Lateral roots were similarly sampled at the mid- and terminal portions. Eighteen to twenty root segments were sampled per plant. The number of roots colonized by the strains in question were determined by plated on the selective and differential media described in the text, and identity of strains was verified by isozyme electrophoresis.

DISCUSSION

Seedsmen are interested in obtaining effective biological seed treatments. They are particularly interested in obtaining broad spectrum seed protectants to fill the role of captan or thiram. The future of captan is questionable due to unresolved questions concerning its long-term health effects. Moreover, restrictions on application of these chemicals and disposal of unused treated seeds in several states make use of these materials difficult.

For biological seed treatments to fill the niche described above, they must be consistently effective against a range of pathogens. In the past, biological seed treatments have been both more variable and less effective than chemical fungicide treatments, (Kommendahl et al, *Protect. Ecol.*, 3:55–61; Ruppel et al, *Crop Protect.*, 2:399–408). Moreover, individual strains of Trichoderma have been shown to be effective against only one or two pathogens. A wide spectrum of activity is not known for specific strains, although the entire genus, together with Gliocladium, does control many pathogens. In the present work, it was demonstrated that all strains tested will control *Pythium ultimum, Phizoctonia solani, Fusarium graininearum*, and *Sclerotium rolfsii*. In other work, it has been shown that T12 will control *Alternaria raphani* and *A. brassicicola* (Vannacci and Harman, *Can. J. Microbiol.*, 33:850–856). Thus, these strains appear to have the wide spectrum of activity useful for a general purpose seed treatment or for other applications.

Solid matrix priming also markedly enhanced the ability of the Trichoderma strains to control Pythium spp. In the seedling assays, protection of nearly all crops was greater in the presence of priming than without. In field trials, protection of peas by the strains without priming was negligible but was evident when seeds were treated using this procedure. Effects of priming on stand establishment with sweet corn were less pronounced; in the first trial with Florida Staysweet, emergence in the absence of T12 was reduced by priming. The lesser results of priming on this crop relative to peas in the field are consistent with the seedling assays which demonstrate that *P. ultimum* reduces stands less with sweet corn than with other crops tested. Priming had little effect on the ability of the biocontrol strains to protect against *S. rolfsii*, and with *R. solani*, appeared to reduce the effectiveness of the Trichoderma strains.

The level of protection of the biological seed treatments on peas in the field appeared modest. However, the conditions were quite unfavorable for the biocontrol strains, and for them to show any activity is encouraging. In the first trials, soils were cold, with the lowest temperatures at or below the minimum temperatures for growth of these strains. Furthermore, the pathogen was added into the planting furrow directly onto the seeds. Under these conditions, a toxicant, e.g. metalaxyl, would appear more effective than a biocontrol strain whose protective ability may depend upon more subtle mechanisms, (see Chet, Trichoderma - application mode of action, and potential as a biocontrol agent of soilborne plant pathogenic fungi pp 137–160. In Chet, "Innovative Approaches to Plant Disease Control." John Wiiey & Sons, New York).

Strain differences in ability to protect seeds against the various pathogens was evident. In general strain T95 performed the poorest. These differences may lie in its intrinsic ability to control the pathogens in question. However, it was shown earlier that the Trichoderma strain from which T95 was derived by mutation is poorly adapted to compete in New York soils (10). Thus, the poorer activity may be more reflective of this strain's poor adaption to the soil in which it was tested.

The progeny strains were somewhat better seed protectants than either T12 or T95 in some tests with Pythium, but these increased levels of protection were not large. It is difficult to see improvement with most tests with Pythium, however, because, particularly with priming, there is little room for improvement. The stands plus the standard deviations frequently exceed 100%, even though the disease potential is quite high. Thus, one difficulty in developing improved strains is to devise tests that allow detection of improved strains when the level of protection with existing strains and systems already is substantial.

At least as important as seed protection is the ability of strains to protect and colonize roots, and to otherwise provide benefits for the active life of the crop. The protoplast fusion progeny appear to be highly improved in this regard. They protected cucumber roots in the seedling assay test, which suggest better root colonizing ability. This ability was confirmed in the field trials with peas. Strains 1295-22 and 106 colonized nearly all of the pea root segments tested, even when the plants were mature. Strains T12 and T95 were poorer in this ability. It could not be determined on the basis of the data what the relative contribution to root colonization of actual ability of the strains to grow directly on the root surface (i.e. rhizosphere or rhizoplane competence) relative to their transfer due to mass movement of propagules in water percolating through soil. The latter method of movement apparently did occur, and indicated by colonization of roots by 1295-22 or 106 in block trials of non-treated peas adjacent to those treated with these fungi.

Taken together, the data suggest that the seed treatment systems we have developed (improved seed treatment procedures together with improved strains) are attractive candidates to augment or replace existing broad spectrum fungicides (i.e. thiram or captan). They have the ability to protect against a range of pathogens and are consistently as effective as thiram, at least in seedling trials. In addition, they offer advantages not obtainable with chemical seed protectants, especially the ability to colonize and protect roots.

We claim:

1. A biologically pure Trichoderma strain selected from the group consisting of 1295-7 (ATCC 20846), 1295-74 (ATCC 20848), 1295-22 (ATCC 20847) and 1295-106 (ATCC 20873).

2. The biologically pure Trichoderma strain as in claim 1 selected from the group consisting of 1295-7, 1295-74 and 1295-22.

3. The biologically pure Trichoderma strain as in claim 1 which is 1295-22.

4. The biologically pure Trichoderma strain as in claim 1 which is 1295-106.

* * * * *